(12) United States Patent
Sinofsky (10) Patent No.: US 6,270,492 B1
(45) Date of Patent: *Aug. 7, 2001

(54) PHOTOTHERAPEUTIC APPARATUS WITH DIFFUSIVE TIP ASSEMBLY

(75) Inventor: Edward L. Sinofsky, Dennis, MA (US)

(73) Assignee: CardioFocus, Inc., Norton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/390,964

(22) Filed: Sep. 7, 1999

Related U.S. Application Data (63) Continuation-in-part of application No. 08/991,130, filed on Dec. 16, 1997, now Pat. No. 5,947,959, which is a continuation-in-part of application No. 08/827,631, filed on Apr. 10, 1997, now Pat. No. 5,908,415, which is a continuation of application No. 08/303,605, filed on Sep. 9, 1994, now abandoned.

(51) Int. Cl.⁷ .................................................. A61B 17/37
(52) U.S. Cl. ................................. 606/15; 606/7; 606/13
(58) Field of Search .................................. 606/7, 13–17

(56) References Cited

U.S. PATENT DOCUMENTS

| | | | |
|---|---|---|---|
| 5,151,096 | 9/1992 | Khoury | 606/15 |
| 5,151,097 | 9/1992 | Daikuzono | 606/15 |
| 5,163,935 | 11/1992 | Black et al. | 606/17 |
| 5,219,346 | 6/1993 | Wagnieres et al. | 606/16 |
| 5,431,647 | 7/1995 | Purcell, Jr. et al. | 606/16 |
| 5,441,497 | 8/1995 | Narciso, Jr. | 606/15 |
| 5,536,265 | 7/1996 | van den Bergh et al. | 606/2 |
| 5,643,253 | 7/1997 | Baxter et al. | 606/17 |
| 5,908,415 | * 6/1999 | Sinofsky | 606/7 |

FOREIGN PATENT DOCUMENTS 9607451    3/1996   (WO) .

* cited by examiner

*Primary Examiner*—Robert L. Nasser
(74) *Attorney, Agent, or Firm*—Thomas J. Engellenner; Nutter, McClennen & Fish, LLP (57) ABSTRACT

An optical transmissive, light-diffusing, fiber tip assembly having a radiation-scattering particles incorporated therein and a reflective end surface is disclosed for use in phototherapy. As radiation propagates through the fiber tip, a portion of the radiation is scattered in a cylindrical (or partially cylindrical) pattern along the length of the fiber tip. Radiation which is not scattered during this initial pass through the tip is reflected by at least one surface of the assembly and returned through the tip. During this second pass, the remaining radiation (or at least a major portion of this returning radiation) again encounters the scatterers which provide further radial diffusion of the radiation. Preferably, the scattering medium and the reflective end cap interact to provide a substantially uniform axial distribution of laser radiation over the length of the tip apparatus. Methods and devices are also disclosed in which a dielectric structure is operatively coupled to phototherapeutic instrument to reflect light without substantial heating. The invention is particularly useful in light diffusive tip assemblies for phototherapy that have components which increase in temperature after prolonged exposure to light, such as mirrors and metallic structures incorporated into such diffusers to facilitate radiographic or fluoroscopic imaging during a therapeutic procedure.

25 Claims, 8 Drawing Sheets

PHOTOTHERAPEUTIC APPARATUS WITH DIFFUSIVE TIP ASSEMBLY

REFERENCE TO RELATED APPLICATIONS

This application is a continuation-in-part of U.S. patent application Ser. No. 08/991,130, incorporated herein by reference and filed Dec. 16, 1997 now U.S. Pat. No. 5,947 959, was a continuation-in-part of U.S. patent application Ser. No. 08/827,631, incorporated herein by reference and filed Apr. 10, 1997 (now U.S. Pat. No. 5,908,415), which was a continuation of U.S. patent application Ser. No. 08/303,605, incorporated herein by reference and filed Sep. 9, 1994 (now abandoned).

BACKGROUND OF THE INVENTION

The technical field of this invention is phototherapy and, in particular, methods and devices which employ optical fibers or other flexible light waveguides to deliver radiation to a targeted biological site.

Fiber optic phototherapy is a increasing popular modality for the diagnosis and/or treatment of a wide variety of diseases. For example, in surgery, infrared laser radiation will often be delivered to a surgical site via a hand-held instrument incorporating an optically transmissive fiber in order to coagulate blood or cauterize tissue. Similar fiber optic delivery systems have been proposed for endoscopic or catheter-based instruments to deliver therapeutic radiation to a body lumen or cavity. U.S. Pat. No. 4, 336,809 (Clark) and U.S. Reissue Patent No. RE 34,544 (Spears) disclose that hematoporphyrin dyes and the like selectively accumulate in tumorous tissue and such accumulations can be detected by a characteristic fluorescence under irradiation with blue light. These patents further teach that cancerous tissue that has taken up the dye can be preferentially destroyed by radiation (typically high intensity red light) that is absorbed by the dye molecules during phototherapy.

Others have proposed the use of fiber-delivered radiation to treat artherosclerotic disease. For example, U.S. Pat. No. 4,878,492 (Sinofsky et al.) discloses the used of infrared radiation to heat blood vessel walls during balloon angioplasty in order to fuse the endothelial lining of the blood vessel and seal the surface. Another application of fiber-delivered radiation is disclosed in U.S. Pat. No. 5,053,033 (Clarke) which teaches that restenosis following angioplasty can be inhibited by application of UV radiation to the angioplasty site to kill smooth muscle cells which would otherwise proliferate in response to angioplasty-induced injuries to blood vessel walls.

Nonetheless, a number of problems limit the expanded use of fiber-optic phototherapy. Typically, an optical fiber emits light from only its end face. Thus, the emitted light tends to be focused or at best divergent in a conical pattern and, therefore, exposes only a small region directly in front of the fiber's distal end. The small exposure area limits the power available for phototherapy since overheating of the target tissue must often be avoided.

Although "sideways-emitting" fibers have been proposed to permit greater flexibility in phototherapy, this approach still does not allow uniform irradiation of large volumes of tissue and can also be ill-suited for applications where circumferential uniformity is desired. Because sideways-emitting fibers expose limited regions, they do little to alleviate the problem of "hot spots" which limit the intensity of radiation which can be delivered via the fiber to the treatment site.

Others have proposed diffusive tips for optical fibers to enlarge the region which can be irradiated and/or reduce the potential for overexposure. However, diffusive tips have not been satisfactory for many therapeutic purposes because of their complexity of manufacture and/or because the radiation may not be scattered uniformly enough to alleviate the problem of "hot spots." Prior art diffusive tip structures have not be capable of delivering high power radiation, e.g., on the order of ten watts or more, to facilitate photocoagulation therapy or the like.

There exists a need for better apparatus for fiber-optic phototherapy. In particular, diffusive fiber tip assemblies which can provide circumferential (or large angle) exposure regions in radial directions (e.g., sideways) relative to the fiber axis without hot spots would satisfy a long-felt need in the art. Moreover, diffusive assemblies which illuminate or irradiate an azimuthal angle of less than 360° would meet a particularly important need in the field of minimally-invasive, phototherapeutic surgery. In addition, diffusive fiber tip assemblies which can extend the longitudinal extent of irradiation and provide greater flexibility during use would likewise satisfy a need in phototherapy.

In addition, there exists a need for controlling or reduced unwanted heating effects during phototherapy. Typically, light can be delivered to the site of the desired photothera-peutic reaction by inserting a fiber-optic cable into a patient and maneuvering it to the site of the desired photochemical reaction. The position of the fiber's tip can be monitored by including a metallic structure at the tip and monitoring the position of the metallic structure, either visually or by x-ray fluoroscopy. Additionally, metallic structures are sometimes used to reflect light and to thereby control the illumination field within the patient.

When illuminated by light, these metallic structures absorb a small, yet significant amount of optical energy and reradiate it as heat. Since the metallic structures of photo-therapeutic instruments are generally in contact with or proximate to surrounding tissue, the rise in temperature of these structures can inflict heat-induced tissue damage on surrounding tissue or melt catheters in the vicinity of the fiber's tip.

Accordingly, there exists a need for better methods and apparatuses for preventing the metallic structure in photo-therapeutic devices from being heated excessively by incident light during use.

SUMMARY OF THE INVENTION

Methods and apparatus are disclosed for diffusing radiation from a optical fiber to provide a larger exposure area for phototherapy. The methods and apparatus are particularly useful as part of a fiber optic-based medical laser system. The present invention can further provide substantially uniform energy distribution to a major portion of the exposure area. The invention is especially useful in constructing and implementing circumferential and/or sideways-emitting diffusive tip assemblies for optical fibers to direct laser radiation in a radially outward pattern relative to the fiber's axis. As used herein the term "optical fiber" is intended to encompass optically transmissive waveguides of various shapes and sizes.

In one aspect of the invention, an optical transmissive fiber tip structure is disclosed having a radiation-scattering particles and a reflective end. As radiation propagates through the fiber tip, the radiation is scattered. Each time the radiation encounters a scatterer particle, it is deflected until some of the radiation exceeds the critical angle for internal reflection and exits the tip Radiation which is not emitted during this initial pass through the tip is reflected by at least one end surface and returned through the tip. During this second pass, the remaining radiation (or at least a major portion of this returning radiation) again encounters the scatterers which provide further radial diffusion of the radiation.

In one embodiment, a diffusive tip assembly is disclosed for diffusing radiation from an optical fiber. The tip assembly includes a light transmissive, tubular housing alignable with, and adapted to receive, the distal end of the fiber and serve as a waveguide for light propagating through the fiber. The assembly further includes a reflective end cap and a light scattering medium disposed therein such that light propagating through said fiber enters the scattering medium and a portion of the light escapes outward through the housing, and another portion passes through the scattering medium and is reflected by the end cap for retransmission through said scattering medium.

The reflective surfaces of the apparatus can also be modified to effect non-cylindrical or non-spherical exposure patterns. Reflective structures are disclosed which control the azimuthal extent of the light emitted from the tip. These techniques and structures permit, for example, 270 degrees, 180 degrees or even smaller angles of azimuthal exposure. The term "large angle exposure" is used herein to describe partially cylindrical (or partially spherical) exposure patterns having a azimuthal angle of more than about 90 degrees.

In another aspect of the invention, the amount of incorporated scatterers and/or the length of the diffusive tip can be controlled such the diffusion of the radiation beam during the initial and reflected paths are complementary. By proper choice of such parameters, the cumulative energy density or fluence along at least a portion of the length of fiber tip can be rendered uniform. The term "substantially uniform" is commonly used in the field of fiber optic phototherapy to describe a light diffusers that possess a degree of uniformity of emitted light of +/−30 percent of the average intensity of light emitted from a diffusive tip assembly. The invention thus provides a mechanism for substantially uniform axial and/or cylindrical irradiation of biological structures and the like.

In a further aspect of the invention, bundling techniques and configurations are disclosed for extending the axial extent of diffusive irradiation and/or for permitting selective activation of fibers or fiber subsets to effect site-specific phototherapy of regions or sectors of a patient's tissue in the vicinity of the optical fiber tip. Such bundled systems can also be used to deliver two or more different wavelengths of radiation to the treatment site and thereby provide synergistic effects from multiple wavelengths of therapy, or permit diagnostic and therapeutic radiation of different wavelengths to be delivered in a single procedure.

In yet another aspect of the invention, novel materials and structures are disclosed for diffusive tip assemblies to alleviate or reduce the potential for contact-adhesion between the tip and nearby tissue segments. This aspect of the invention is particularly useful in connection with endoscopic and/or catheter-based phototherapy to ensure that the diffusive tip does not bond accidentally to the body lumen or blood vessel wall during procedures. In one embodiment, fluoropolymer materials, such as Teflon® materials and the like, are disclosed as preferred materials fo the tip enclosure and/or the outer cladding or coating to inhibit contact-adhesion between the tip assembly and biological tissue during procedures. Most preferably, the Teflon® material is a Teflon® FEP material (a polyperfluoroethylene-propylene copolymer). Other Teflon® materials such as Teflon® PFA (a polytetrafluoroethylene polymer with perfluoroalkoxy side chains) and Teflon® PTFE (polytetrafluoroethylene) also can be useful in certain applications.

In a further aspect of the invention, novel scatterer structures are disclosed which permit the diffusion of ultraviolet (UV) and infrared (IR) radiation with higher efficiency than prior art structures. Liquid-filled scattering assemblies and, in particular, structures employing deuterium oxide and other heavy water solutions are disclosed which transmit IR light with low losses and minimal tip heating. Distilled water suspensions of scatterers are disclosed for UV light delivery.

In yet a further aspect of the invention, novel treatment protocols are disclosed for minimally invasive phototherapeutic surgery. For example, protocols for the treatment of prostate cancer and similar diseases are disclosed in which a diffusive tip assembly is placed in the vicinity of the cancerous organ or body structure and diffuse light is used to heat and selectively destroy cancerous or dysplastic tissue. In addition, the present invention can be use for the closure of body ducts and/or the reconstruction of competent junctures between ducts or valves that have been malformed or damaged. Moreover, photoactivation of pharmacological agents, implanted structures, or suture materials can all be advantageously effected with the diffusive assemblies of the present invention.

The structures disclosed herein represent a substantial step forward in the delivery of therapeutic radiation to remote treatment sites. The diffusive assembly designs of the present invention permit the delivery of radiation at power levels on the order of tens of Watts or more. In fact, diffusive tip assemblies have been successfully constructed to deliver over 100 Watts of power in a diffuse pattern to a treatment site, allowing the clinician to perform therapy rapidly and uniformly to a large volume of tissue In addition, methods and devices are disclosed in which a dielectric structure is operatively coupled to a phototherapeutic instrument to reflect light without substantial heating. The invention is particularly useful in light diffusive tip assemblies for phototherapy that have components which increase in temperature after prolonged exposure to light, such as metallic plugs or coatings typically located at the end cap of the diffusive tip assembly to terminate light propagation, and also in metallic structures incorporated into phototherapeutic instruments to facilitate radiographic or fluoroscopic imaging and direct visualization of the diffusive tip assembly during a therapeutic procedure.

Typically, diffusive tip assemblies include a light-transmissive housing forming a chamber filled with a diffusive medium and extending along a longitudinal axis. At its proximal end, the housing is adapted to receive a fiber-optic cable. A reflector component is often disposed at the distal end of the chamber. In the present invention, the reflector component includes a dielectric reflector structure.

The dielectric reflector structure of the invention includes at least one dielectric layer having an interface at its proximal end with the diffusive medium and forming a proximal reflecting surface. The distal end of the dielectric layer forms a distal reflecting surface at the interface between the dielectric layer and either a second dielectric layer or a light-transmissive substrate layer. The substrate layer is adjacent to a thermally susceptible surface such as a conducting surface. The dielectric structure essentially creates a gradient in the index of refraction. By proper choice of materials and their thicknesses, the dielectric gradient structure achieves nearly complete reflection without substantial heating. As used herein, the terms "nearly complete reflection" and/or "complete reflection" are intended to encompass reflectivity ratios of 95 percent or greater. Similarly, the term "without substantial heating" is intended to encompass temperature rises during operation that do not exceed 60° C.

In the operation of a light diffuser according to the invention, light carried by the fiber-optic cable enters the chamber at its proximal end and propagates distally through the diffusive medium in the chamber toward the dielectric reflector structure. At the dielectric reflector structure, the proximal reflecting surface reflects a portion of the light incident thereon back into the diffuser and transmits the remaining portion of the light incident thereon distally, thereby attenuating the intensity of illumination incident on the distal reflecting surface. Since the dielectric layer typically has a purely real index of refraction, no heating occurs in the dielectric.

This incident light transmitted through the proximal reflecting surface is then reflected by the distal reflecting surface of the dielectric layer. The position of this distal reflecting surface relative to the proximal reflecting surface is chosen such that the light reflected by the distal reflecting surface and the light reflected by the proximal reflecting surface constructively interfere with one another. This increases the intensity of the light propagating proximally and reduces the intensity of the light propagating distally.

Where the distal reflecting surface is an interface between the dielectric layer and a thermally susceptible surface, such as a conducting surface, it is apparent that, because the proximal reflecting surface transmits only a portion of the light incident thereon distally toward the thermally susceptible surface, the intensity of the light incident on the thermally susceptible surface is attenuated by the reflection at the proximal reflecting surface. As a result, there is less energy available for the undesired heating of the thermally susceptible surface.

Although the scope of the invention includes the case of a single dielectric layer, as set forth above, such a configuration may not result in sufficient attenuation of the optical energy incident on the thermally susceptible surface. Consequently, in one preferred embodiment, a plurality of adjacent dielectric layers is interposed between the diffusive medium and the thermally susceptible surface. Each such dielectric layer forms a proximal reflecting surface which proximally reflects a portion of the field incident thereon. For each such dielectric layer, a remaining portion of the field incident thereon is transmitted distally towards either an adjacent dielectric layer or, in the case of the most distal such layer, towards a thermally susceptible surface. The cumulative effect of a plurality of adjacent dielectric layers on the light passing therethrough is a significant attenuation of the light intensity illuminating the thermally susceptible surface resulting from each of the reflections occurring at each dielectric interface.

In another embodiment of the invention, the thermally susceptible surface is an annular structure. In this embodiment, the first reflection can be provided by an annular interface between the diffusive medium and a cylindrical dielectric layer interposed between the illumination source and the annular, thermally susceptible surface. Succeeding reflections can then be provided by annular interfaces between adjacent cylindrical dielectric layers. In this embodiment, the succession of adjacent dielectric layers interposed between the illumination source and the thermally susceptible surface forms a tube having a lumen filled with the diffusive medium.

The invention will next be described in connection with certain preferred embodiments. However, it should be clear that various changes and modifications can be made by those skilled in the art without departing from the spirit and scope of the invention.

BRIEF DESCRIPTION OF THE DRAWINGS

The invention may be more fully understood from the following description when read together with the accompanying drawings in which.

DETAILED DESCRIPTION

Figure 1:
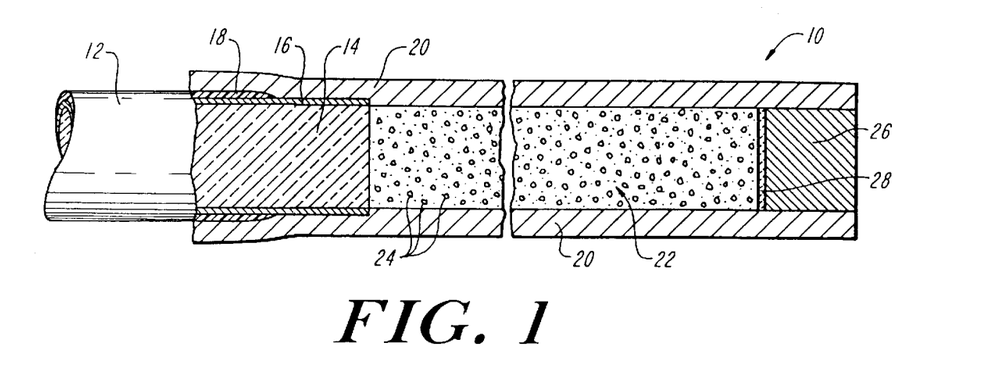
FIG. 1 is a cross-sectional illustration of a phototherapeutic apparatus incorporating an optical fiber and a diffusive tip assembly in accordance with the present invention.

In FIG. 1 an optical fiber diffusive tip assembly 10 is shown including an optical fiber 12 having a light-transmissive core 14, a cladding 16, and an outer buffer coating 18. The end face of fiber core 14 is inserted into a housing 20 which contains scattering medium 22 with individual scatterer particles 24. Preferably, the medium 22 has a greater refractive index then the housing 20. At the distal end of the housing 20, an end plug 26 is disposed with a mirror reflector 28.

Light propagating through optical fiber core 14 is transmitted into the scatterer medium 22 and scattered in a cylindrical pattern along the length of the assembly 10. Each time the light encounters a scatterer particles, it is deflected and, at some point, the net deflection exceeds the critical angle for internal reflection at the interface between the housing 20 and medium 22. When this happens, the light will exit. Light which does not exit during this initial pass through the tip is reflected by the mirror 28 and returned through the tip assembly. During the second pass, the remaining radiation (or at least a major portion of this returning radiation) again encounters the scatterers 22 which provide further circumferential diffusion of the light.

Figure 2:
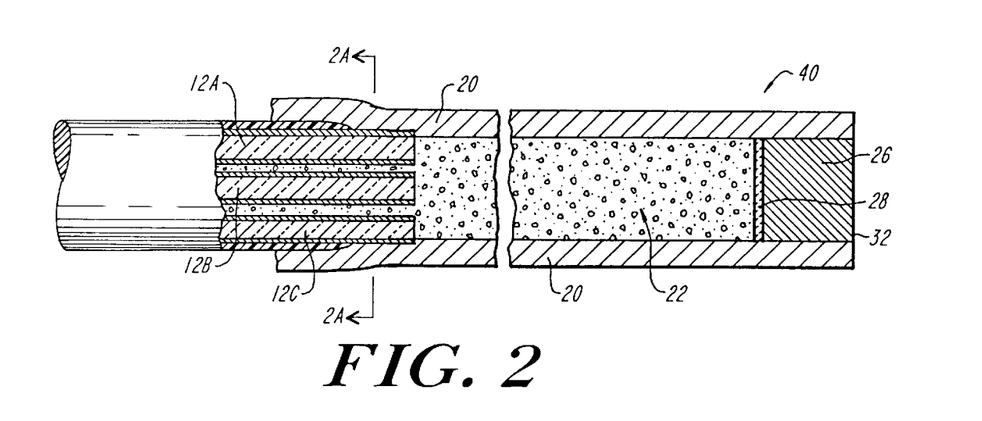
FIG. 2 is another cross-sectional illustration of a phototherapeutic apparatus in accordance with the present invention incorporating a plurality of optical fibers and a diffusive tip assembly.
Figure 2A:
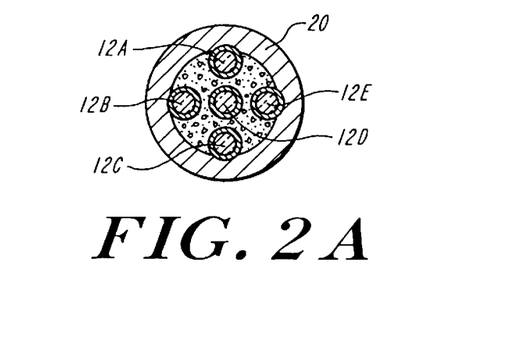
FIG. 2A is a cross-sectional view of the optical fiber diffusive tip assembly of FIG. 2 taken along the line A—A of FIG. 2.

In FIGS. 2 and 2A, another diffusive tip assembly 40 is shown having essentially identical elements to those shown in FIG. 1, except for the disposition of a bundle of optical fibers 12A–12E. The individual cores of the fibers are exposed and transmit light into the scatterer medium 22.

FIG. 2A is a cross-sectional view of the device of FIG. 2 showing the placement of the bundle of optical fibers 12A–12E and the surrounding tube 20, scatterer medium 22 and reflector 28.

Figure 3:
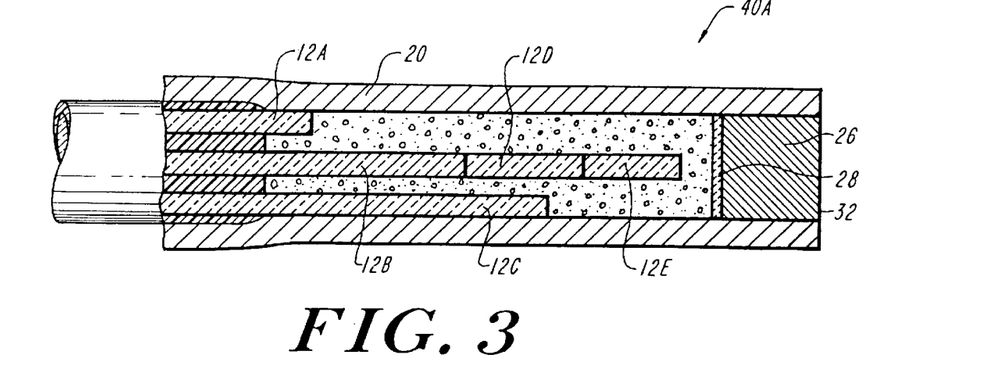
FIG. 3 is another cross-sectional illustration of a phototherapeutic apparatus in accordance with the present invention incorporating a plurality of optical fibers and a diffusive tip assembly in which the fibers have different terminal points within the assembly.
Figure 3A:
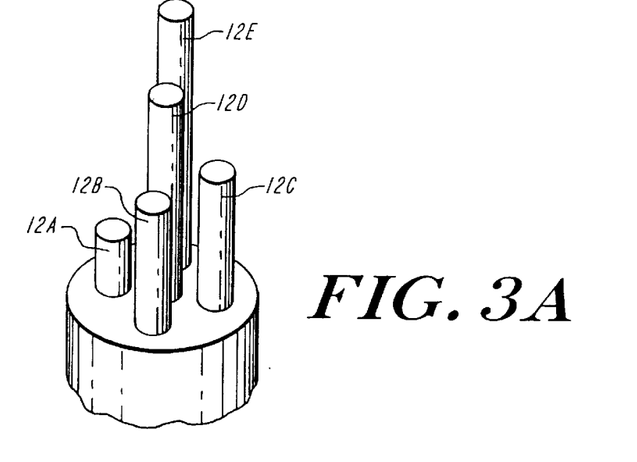
FIG. 3A is perspective view of the end portions of the optical fibers of FIG. 3.

In FIGS. 3 and 3A, another diffusive tip assembly 40A is shown again having essentially identical elements to those shown in FIG. 1, except for the disposition of a bundle of optical fibers 12A–12E. The individual cores of the fibers are exposed and transmit light into the scatterer medium 22, but the individual fibers terminate at different locations within housing 20, thereby permitting extended axial diffusion.

FIG. 3A is a perspective view of the fiber bundle of FIG. 3 showing the placement of the bundle of optical fibers 12A–12E within the housing.

Figure 4:
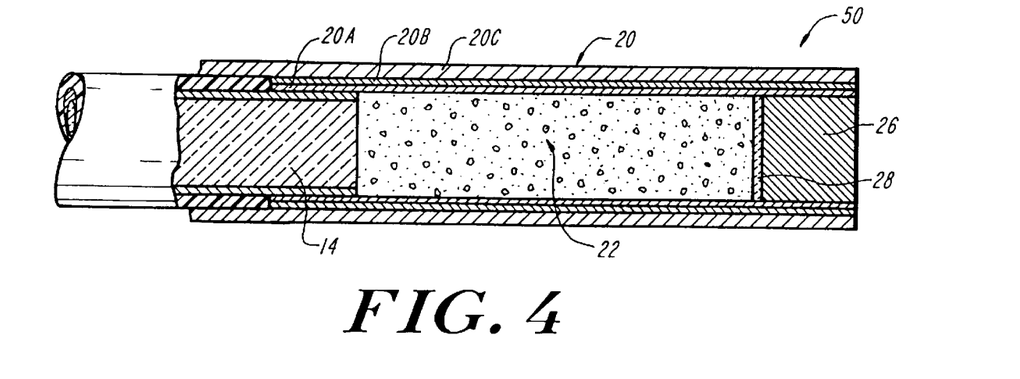
FIG. 4 is another cross-sectional illustration of a phototherapeutic apparatus in accordance with the present invention incorporating a multilayer laminated scatterer tube element.

In FIG. 4, an alternative diffuser tip assembly 50 is shown in which a laminate of multiple layers is used for the scatterer tube 20. Thus, innermost layer 20A encases the scatterer medium 22. Surrounding this innermost layer 20A is an intermediate layer 20B. A third optional layer 20C is then formed about the first two layers 20A, 20B. Such a configuration permits the use of different polymeric tubing materials and/or allows the introduction of pigmented or etched structures as part of tubing 20.

Figure 5:
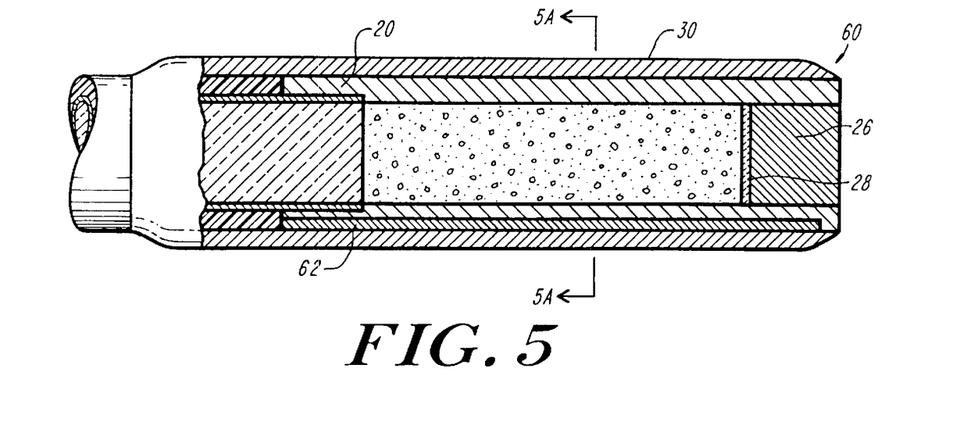
FIG. 5 is another cross-sectional illustration of a phototherapeutic apparatus in accordance with the present invention incorporating a longitudinal reflector to provide azimuthal selectivity in a diffusive tip assembly.
Figure 5A:
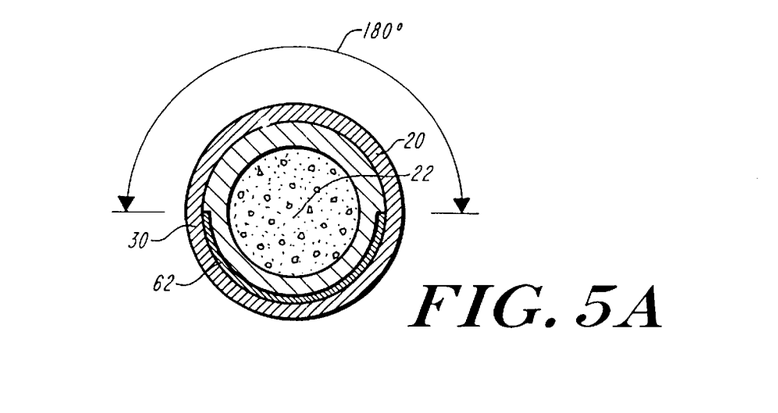
FIG. 5A is a cross-sectional view of the optical fiber diffusive tip assembly of FIG. 5 taken along the line A—A of FIG. 5.

In FIG. 5, another embodiment of a diffusing tip assembly 60 is shown incorporating a longitudinal reflector strip 62. As further illustrated in the cross-sectional section of FIG. 5A, the longitudinal reflector 62 can be formed as a partial layer or foil element within a laminate structure, e.g., between layer 20 and layer 30. The longitudinal reflector 62 illustrated in FIGS. 5 and 5A cooperates with the scatterer medium 22 to create an azimuthal exposure pattern of approximately 180°, although it should be clear that other angles of exposure can be simply achieved by widening (or narrowing) the circumferential extent of the reflector element 62. Various alternative configurations of the reflector can be constructed. For example, the reflector can be disposed on the outside of the housing or can be formed as a coating rather than a foil element. Moreover the longitudinal reflector can be used without reflective end surface 28, if enhanced axial uniformity is not needed.

Figure 6A:
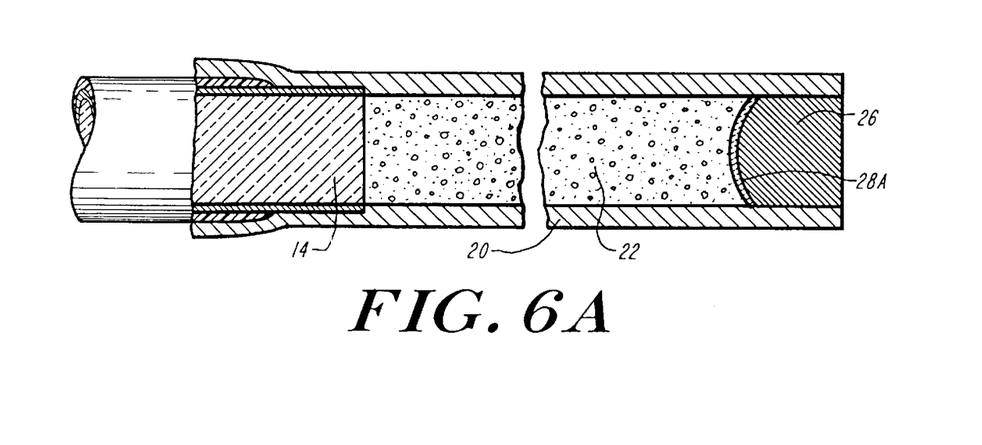
FIG. 6A is a cross-sectional illustration of an alternative reflector design useful in diffusive tip assemblies according to the invention.
Figure 6B:
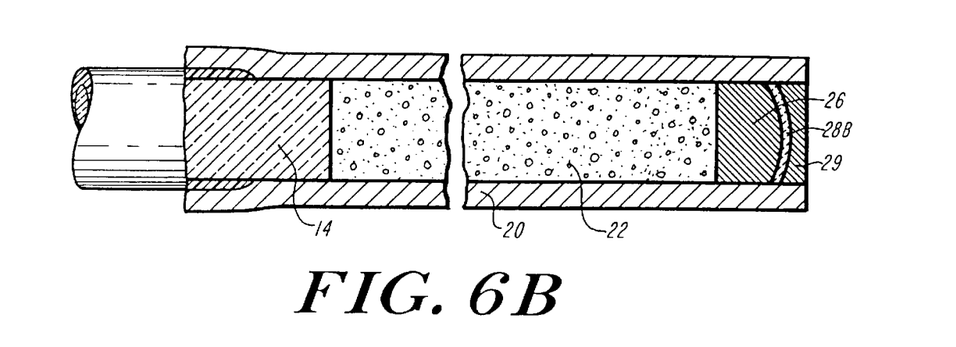
FIG. 6B is a cross-sectional illustration of another alternative reflector design useful in diffusive tip assemblies according to the invention.

In FIG. 6A, an alternative design is shown for the end reflector. As shown, end reflector 28A presents a convex surface to the scattering medium and, thereby, varies the exposure pattern. In FIG. 6B, yet another alternative design for the end reflector is shown, wherein the reflective surface is disposed at the distal rather than proximal end face of the plug 26. In this embodiment, plug 26 is optically transmissive and the reflecting surface 28B is formed as a concave surface. In this embodiment, a filler element 29 may also be disposed at the end of the tube 20.

Figure 7A:
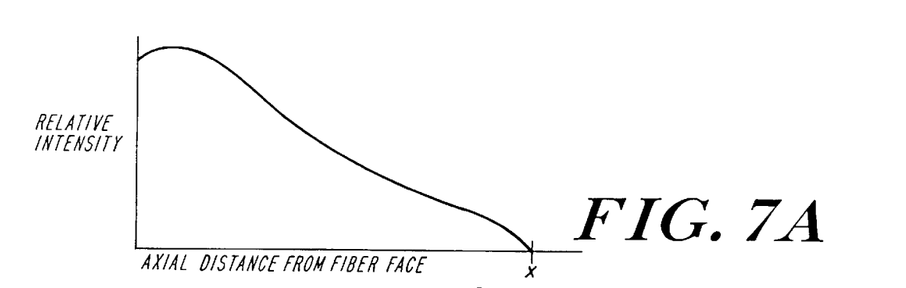
FIGS. 7A, 7B, and 7C are graphs illustrating the relationship between relative intensity and axial distance from the fiber end face for various scatterer loading concentrations.
Figure 7B:
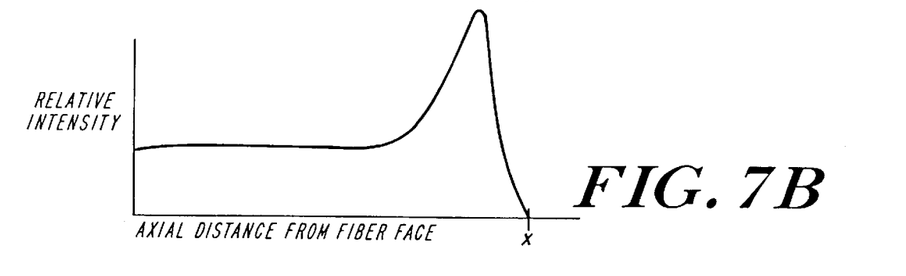
Figure 7C:
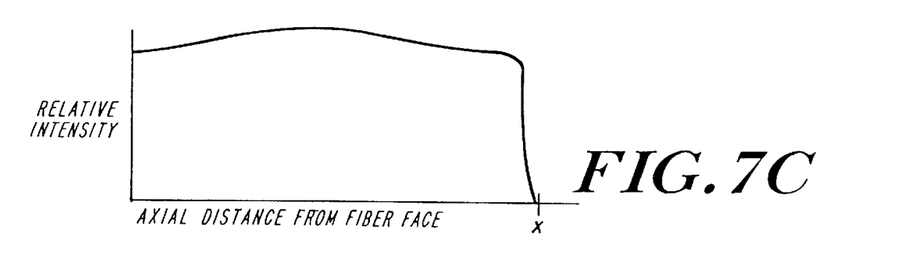

In FIGS. 7A–7C, the effects of different scatterer concentrations on the diffusion pattern of the tip assembly is illustrated. The optimal concentration of scatterer particles incorporated into the scatterer medium will, of course, vary with the diameter of the tube, the length of the tube and the wavelength as well as other factors. Nonetheless, a optimal concentration can be readily determined empirically. FIG. 7A illustrates the situation where too many scatterers have been loaded. Most of the light is diffused immediately upon entry into the scatterer tube. FIG. 7B illustrates the situation where the scatterer medium is too dilute and a bright spot occurs in the vicinity of the reflector. FIG. 7C illustrates a preferred embodiment of the present invention in which the scatterer concentration and mirror location are chosen such that the light is diffused in a substantially uniform axial pattern.

Figure 8:
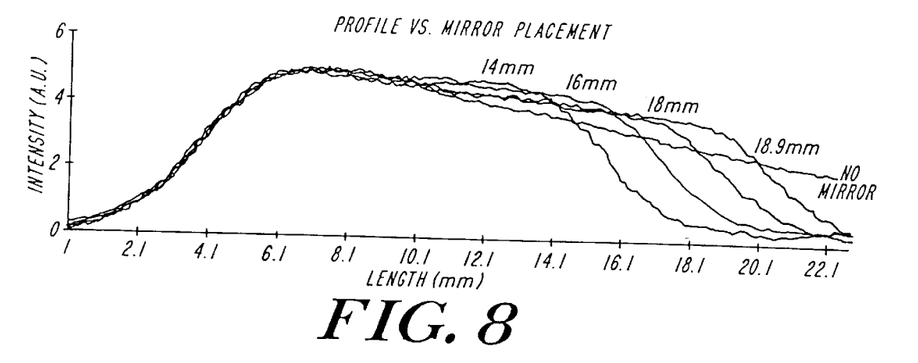
FIG. 8 is graph of intensity versus axial position for various mirror placements in diffusive tip assemblies according to the invention.

It should also be appreciated that the length of the scatterer tube (e.g., the distance between the fiber end face and the reflector) will also affect the uniformity of the diffused radiation. FIG. 8 illustrates how the mirror placement changes the exposure pattern for a given light source, tube diameter and scatterer concentration. As the tube is extended and the distance between the fiber and mirror increases, a drop-off in uniformity is observed. Again, optimal dimensions for a particular application can be determined empirically.

Figure 9:
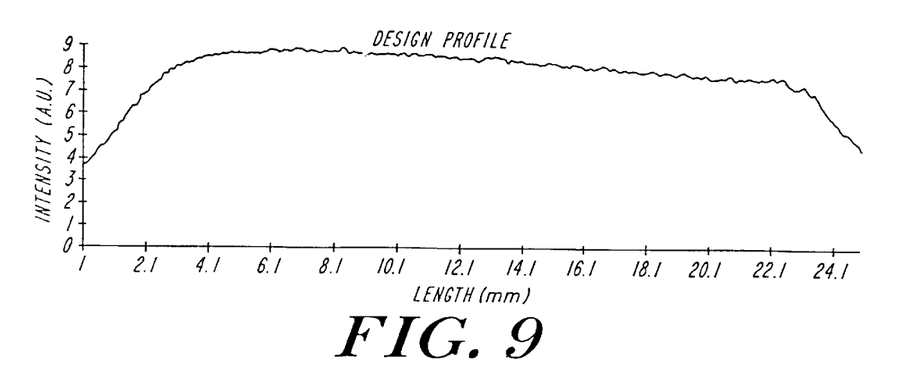
FIG. 9 is graph of intensity versus axial position for an actual diffusive tip assembly according to the invention.

FIG. 9 is graph of intensity for one preferred embodiment of the invention, a fiber tip assembly similar to that shown in FIG. 1 have a Teflon® FEP tubular housing (O.D. of about 0.5 millimeters and I.D. of about 0.25 millimeters) filled with a silicone and titania scatterer composition and capped with an aluminum-coated reflective mirror. The scatterer medium was formulated by mixing 70 parts of clear silicone, Mastersil™ Formula 151-Clear (available from Masterbond, Inc. of Hackensack, N.J.) with one part of titania filled silicone, Mastersil™ Formula 151-White (also available from Masterbond). The result was a diffusive tip assembly which uniformly transmitted red light at about 633 nanometers over its entire length of 25 millimeters.

Figure 10:
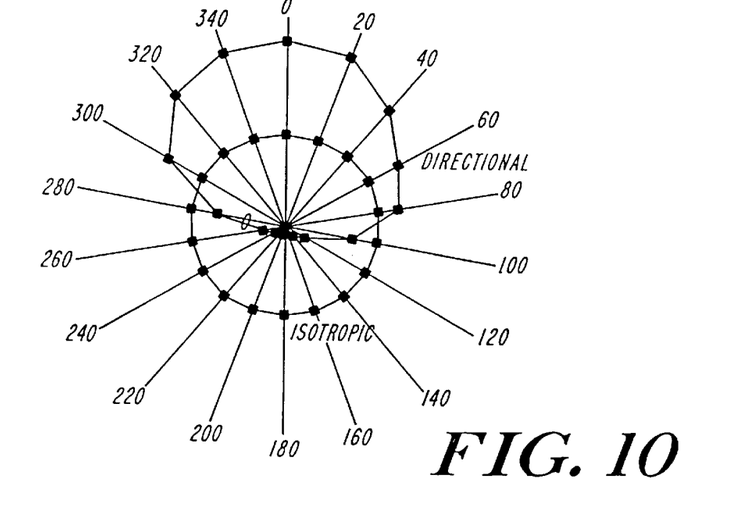
FIG. 10 is a graph of azimuthal intensity distribution of two diffusive tip assemblies according to the invention, one providing a cylindrical exposure pattern and the other providing a semi-cylindrical pattern.

FIG. 10 illustrated the azimuthal exposure patterns for two embodiments of the present invention. The pattern formed by the squares represents intensity of light diffused outwardly with a fiber tip assembly similar to that shown in FIG. 1. This azimuthal exposure pattern is essentially isotropic. The pattern formed by the diamonds represents intensity of light diffused outwardly with a fiber tip assembly similar to that shown in FIG. 5. This azimuthal exposure pattern is essentially semi-cylindrical.

An exemplary manufacturing process suitable for joining a diffuser assembly to a glass-clad or polymer-clad optical fiber having an outer diameter of about 50 to about 1000 micrometers can begin by stripping off the buffer from the end of the optical fiber, e.g., exposing about two or three millimeters of the inner fiber core and its cladding. (It is not necessary to strip the cladding away from the core.) Prior to stripping, the fiber end face preferably should be prepared and polished as known in the art to minimize boundary or interface losses. A transparent tubular structure which will form the housing for the scatterer medium is then slipped over the prepared fiber end and, preferably slid beyond the fiber end. For example, if a tip assembly of about 20 millimeters is desired, the tubing can be about 100 millimeters long and slid over about 75 millimeters of the fiber, leaving an empty lumen of about 25 millimeters in front of the fiber end face. In one preferred embodiment, the housing is Teflon® FEP tubing, available, for example, from Zeus Industries (Raritan, N.J.).

Figure 11:
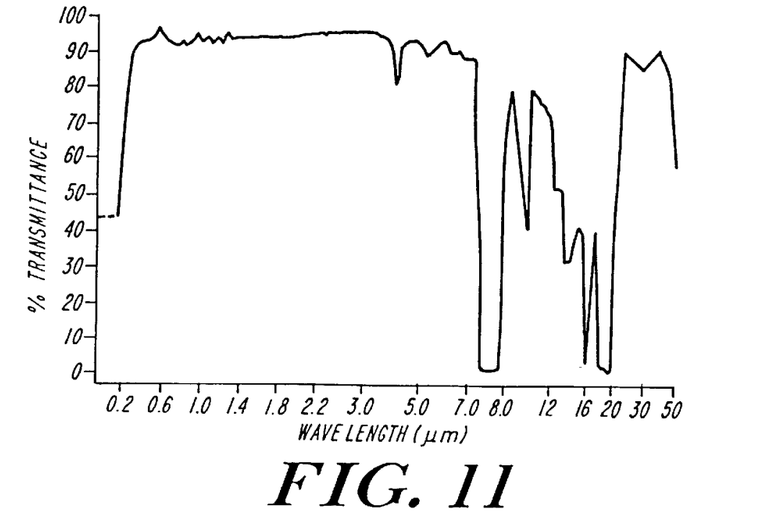
FIG. 11 is graph of the transmission spectrum of Teflon® FEP illustrating the relationship between transmissivity and wavelength.

FIG. 11 illustrates the transmission spectrum of Teflon® FEP, showing that this material is well suited for use as a scatterer-encasing material across a spectrum of light from infrared to ultraviolet.

The assembly is then injected with a scatterer-loaded material, such as a silicone, epoxy or other polymeric material(if a solid diffuser is desired) or a suitable liquid, such as water or a deuterium oxide solution, containing colloidal scatterer particles, such as silica, alumina, or titania, (if a liquid diffuser is desired). As mentioned above, one exemplary scatterer medium can be formulated by mixing 70 parts of clear silicone, Mastersil™ Formula 151-Clear (available from Masterbond, Inc. of Hackensack, N.J.) with one part of titania filled silicone, Mastersil™ Formula 151-White (also available from Masterbond), and a conventional silicone curing or hardening agent. The tube lumen should be completely filled with the silicone, epoxy or other carrier mixture to avoid entrapment of air bubbles. The reflector (e.g., an aluminum, gold or other reflector-coated plug) is inserted into the distal end of the tube. The reflector at the distal end of the scatterer tube can be a deposited metal or dielectric coating. In one preferred embodiment, a room temperature hardening agent is used and the diffuser assembly is simply allowed to solidify overnight.

Optionally, as a final step, an outer Teflon® jacket can be disposed about the apparatus to encase and protect the entire tip assembly including the inner scatterer tube and fiber end. The outer jacket is particularly useful in constructing large azimuthal angle, non-cylindrical diffusers. In such applications, an inner scatterer assembly is constructed and then a reflective strip is disposed along the axis of the assembly to block light diffusion where the housing is covered with the reflector and thereby define a non-cylindrical exposure pattern. The extent of the circumferential coverage by the reflector will determine the azimuthal exposure pattern. The use of an outer jacket also permit a wider variety of tubing choices for the inner component of the scatterer housing. Thus, any transparent material can be used as the inner tube and the outer Teflon® jacket will still ensure that the problem of contact adhesion is minimized.

It should be clear that the manufacturing processes described above are merely illustrative, and various alternative techniques can be practiced to construct the fiber tip assemblies of the present invention. For example, automated extrusion methods and/or injection molding approaches can be employed to mass produce fibers with integral diffusive tip assemblies.

The amount of scatterer incorporated into the diffusive tip assembly will vary with the carrier and the desired length, and can therefore be adjusted to meet particular applications. Different scatterers may be more or less useful in particular applications. Table 1 below illustrates certain relevant characteristics of three different scatterer compositions:

TABLE 1

| Scatterer Characteristics | | |
|---|---|---|
| Scatterer Composition | Density (grams/cc) | Transmission Spectrum (wavelength in micrometers) |
| $TiO_2$ | 4.0 | .45–11 |
| $SiO_2$ | 2.1 | .2–7 |
| $Al_2O_3$ | 3.6 | .2–9 |

In certain applications, it may be desirable to mix two or more scatterer compositions together to achieve blended characteristics.

Liquid scatterer compositions can be used to extend phototherapy into the ultraviolet (UN) and infrared (IR) regions of the spectrum. In particular, structures employing deuterium oxide and other heavy water solutions are useful to transmit IR light with low losses and minimal tip heating. Distilled water suspensions of scatterers are used for UV light delivery.

The above-described manufacturing techniques were used to produce diffusing tips joined to fibers ranging from about 100 to about 600 micrometers in diameter. When fiber bundles are joined to the diffuser tip, the individual fibers can be even smaller, e.g., as small as 25 micrometers in diameter. The cylindrical light-diffusing assemblies produced axial exposure patterns of about 2 cm to about 4 cm in length. The azimuthal exposure angle was either 360° for assemblies resembling FIG. 1 or about 180° for those resembling FIG. 5. Other azimuthal exposure patterns can be obtained by modifying the circumferential extent of the longitudinal reflector strip 62 of FIG. 5. The solid tubes were clear Teflon® and were injected with the above-described mixture of silicone and micron-sized titania. The liquid-filled tubes were similarly constructed but contained a water or $D_2O$ solution loaded with colloidal alumina or silica. A exemplary liquid scatterer composition of colloidal alumina is available as Formulation 12733 from the Johnson Matthey Co. (Seabrook, N.H. Hampshire). In use, it is preferably diluted with water by a factor of about 100:1.

The devices of the present invention can be used for various therapeutic purposes. One application is photodynamic therapy (PDT), a form of light-activated chemotherapy. In this approach, photosensitive dyes are delivered by injection or other vehicles such that the dye is preferentially accumulated in cancer cells. When the cells which have taken up the dye are irradiated at an appropriate wavelength (e.g., with red light), a photochemical reaction occurs that yields radicals (usually singlet oxygen) which poison the cell. Thus, the present invention further encompasses the use of diffused radiation to activate photosensitive dyes. One advantage of the present invention is that it permits PDT at remote treatment sites via a catheter, trocar, hollow needle or other hand held instrument in a minimally invasive manner because diffusive fiber tip assemblies can now be constructed with outer diameters on the order of only a few hundred micrometers.

The present invention also encompasses the use of diffuse radiation in photocoagulation and/or hypodermic therapy of tumors and hyperplasia. For example, the phototherapy apparatuses described above can be used to treat liver, pancreatic or prostate tumors, or benign prostate hyperplasia. The application of diffuse radiation to heat prostate tissue can be used in lieu of transurethral resection of the prostate, balloon dilatation of the prostate or ultrasonic hyperthermia. In particular, the directional probes described above can be especially useful in improving the outcome of prostate treatment by heating more tissue directly in less time, and in distributing irradiation over a larger volume of prostatic tissue, thus increasing the therapeutic heating effects while reducing the risk of overheating damage to surrounding tissue structures such as the sphincter. The invention further permits interstitial laser coagulation of hepatic and pancreatic tumors. The desired effects are achieved by thermal destruction of cancerous tissue by depositing laser radiation via a diffusive fiber tip carrier by a hypodermic needle or similar instrument inserted percutaneously into the tumor. In each of these procedures, therapy can be delivered while the patient is awake; general anesthesia as well as open surgery are avoided.

In heat-based phototherapy techniques, the diffusive fiber tip assemblies of the present invention allow for the formation of large distributed heat sources within the target tissue. The invention significantly alters the rate of heat deposition in tissue, especially in the regions immediately surrounding the fiber tip, where tissue overheating and/or carbonization would limit the effectiveness and inhibit efficient heat transfer. Since the radiation is distributed by the diffuser assembly over a larger volume of tissue, more tissue is heated directly and there is less need to rely on convective or conductive heat transfer through nearby tissue to reach the periphery of the tumor.

Moreover, the materials disclosed herein for the diffusive tips and jackets further enhance the therapeutic effects by permitting high radiation transmission and low absorption, thereby ensuring the tip assembly itself does not overheat during usage. In addition, the use of Teflon® tubes and/or coatings further improve the procedures by avoiding the problem of tip fusion or contact-adhesion between the tip assembly and biological tissue during usage. It has been found that Teflon® FEP materials (polyperfluoroethylene-propylene copolymers) are preferable for most applications because they do not discolor if they are etched prior to loading with the scatterer medium, although Teflon® PFA materials (polytetrafluoroethylene polymers with perfluoroalkoxy side chains) and Teflon® PTFE (polytetrafluoroethylene) and other fluoropolmers may also be useful.

The non-cylindrical, large azimuthal angle diffusers of the present invention are also particularly useful in therapeutic applications. By directionalizing the diffused radiation, the devices disclosed herein can provide therapeutic radiation to large volumes of tissue while also protecting sensitive tissue or biological structures. For example, in prostate treatment, a semi-cylindrical or other large azimuthal angle diffuser can disposed within the urethra and rotated into a position such that the prostate is subjected to phototherapy while the patient's sphincter muscles and/or other tissue regions are largely shielded from irradiation. In addition the non-cylindrical diffusive tip assemblies can be used to deliver a greater dose of radiation to tissue and rotated, if necessary during use to effect a circumferential (or partially-circumferential) scan of the target tissue at the higher intensity level.

The diffusive tip assemblies can be used in various other medical applications, such as, for example, heat-setting of stents, activation of photoreactive suturing materials, curing of prosthetic devices, activation of adhesives for implants and the like.

Figure 12:
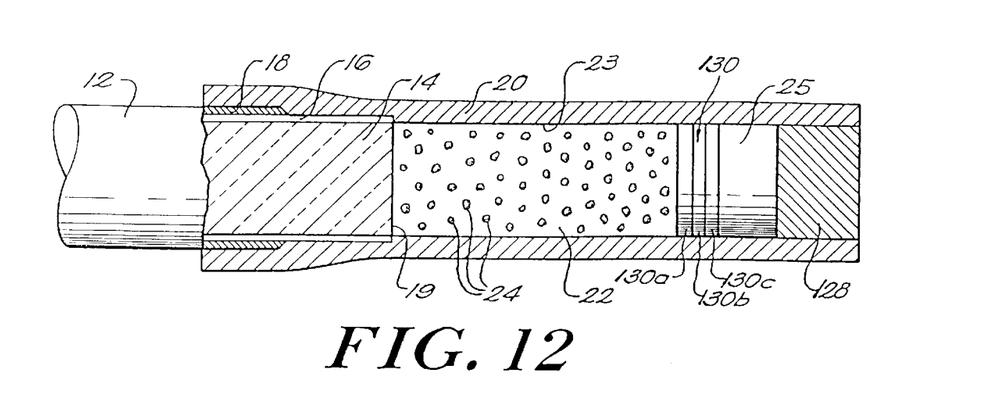
FIG. 12 shows a cut-away view of a diffusive tip assembly according to the invention in which a plurality of dielectric layers is interposed between the diffusive medium and an end plug.

FIG. 12 depicts another diffusive tip assembly which includes an optical fiber 12 having a fiber-optic core 14, a cladding layer 16 circumferentially disposed around the core 14, and an outer buffer coating 18 circumferentially disposed around the cladding layer. The fiber-optic core 14 extends along a longitudinal axis into the proximal end of a light-transmissive housing 20 before terminating in an end face 19. The housing 20 extends along the longitudinal axis past the end face 19 and forms a light-transmissive wall 23 of a tubular chamber having a radius comparable to the radius of the optical fiber 12. The tubular chamber is bounded on its side by the light transmissive wall 23, on its proximal end by the end face 19 of the fiber-optic core 14 and on its distal end by a dielectric reflector 130. A diffusive medium 22 having individual scattering particles 24 suspended throughout fills the tubular chamber 21. Preferably, the diffusive medium 22 has a greater index of refraction than the housing wall 23.

In one preferred embodiment, the diffusive tip assembly shown in FIG. 12 has a Teflon® FEP tubular housing having an outer diameter of about 0.5 millimeters and an inner diameter of about 0.25 millimeters. The transmission spectrum of Teflon® FEP, as shown in FIG. 11, indicates that this material is well suited for use as a housing wall for transmitting a broad spectrum of light, from infrared to ultraviolet.

The tubular chamber is injected with a diffusive medium 22, such as silicone, epoxy or other polymer. A liquid diffusive medium 22 can be used to extend phototherapy into ultraviolet and infrared wavelengths. In particular, deuterium oxide and other heavy water solutions are useful for transmitting infrared light with low losses and minimal heating. In either case, the tubular chamber should be completely filled with the diffusive medium 22 to avoid entrapment of air bubbles.

As noted above, the tubular chamber can filled with a diffusive medium 22 e.g., formulated by mixing seventy parts of clear silicone, Mastersil™ formula 151-Clear (available from Masterbond, Inc. of Hackensack, N.J.) with one part of titania filled silicone, Mastersil™ formula 151-White (also available from Masterbond). This results in a diffusive tip assembly which uniformly transmits light at about 633 nanometers.

The illustrated dielectric reflector 130 comprises a plurality of dielectric interfaces formed by dielectric layers 130a, 130b, 130c on a substrate layer 25. The substrate layer 25 is a light-transmissive layer such as glass. To ensure constructive interference within the dielectric layer, each dielectric layer is a quarter wavelength thick as measured by the wavelength within the dielectric layer (i.e. nd=λ/4 where n=index of reflection and d=thickness of dielectric layer). It is apparent, however, that thicknesses that are integer multiples of a quarter wavelength will likewise produce the desired constructive interference within the dielectric layer. In one preferred embodiment, the dielectric reflector 130 includes fifteen to thirty dielectric layers.

Preferably, the proximal dielectric layer 130a has a dielectric constant larger than the dielectric constant of the diffusive medium 22. The dielectric constants for succeeding dielectric layers 130b, 130c need only be different from each other so as to ensure the existence of a reflection at the dielectric interfaces. In one preferred embodiment, the dielectric used for the first, or proximal, dielectric layer 130a is used for all odd number layers and the dielectric used for the second dielectric layer 130b is used for all even number layers. Although any dielectric material having the foregoing properties can be used, one preferred embodiment employs two dielectrics that are rare earth oxides, Alternatively, the dielectric can be selected from a group consisting of silicon dioxide, titanium dioxide, and silica oxide.

Light propagating distally along the longitudinal axis through the fiber-optic core 14 enters the diffusive medium 22 at the proximal end of the tubular chamber and scatters off the individual scattering particles 24 before reaching the light-transmissive wall 23 of the housing. If this scattered light is incident on the wall 23 at an angle exceeding the critical angle for internal reflection for the interface between the wall 23 and the diffusive medium 22, the light exits the diffusive tip assembly.

Any light that does not exit the diffusive tip assembly continues toward the distal end of the tubular chamber where it impinges upon the proximal dielectric layer 130a. The proximal dielectric layer 130a reflects a portion of the light incident thereon back toward the proximal end of the tubular chamber 21. The remaining portion of this incident light propagates through the proximal dielectric layer 130a until it reaches the second dielectric layer 130b. At the second dielectric layer 130b, a portion of the remaining incident light is reflected back toward the proximal end of the tubular chamber and a further remaining portion continues to propagate distally through the second dielectric layer 130b.

The sequence of reflections at each dielectric interface proceeds as described above until light propagates through the distal dielectric layer 30c and reaches a metal slug 28. The metal slug, which is preferably a gold slug, then reflects a portion of the light incident thereon back toward the proximal end of the tubular chamber. The remaining portion of the incident light is converted into heat at the metal slug 128. It is the reduction of this heat and of the accompanying risk of heat-induced tissue damage that is the object of this invention.

It is apparent that as light propagates distally through the dielectric reflector 130, the magnitude of the Poynting vector associated with the light wave decreases. In the apparatus described above, the magnitude decreases stepwise with each reflection at each dielectric interface. As a result, the magnitude of the Poynting vector associated with light propagating through the substrate layer 25 adjacent to the metal slug 128, and therefore the power incident on the metal slug 128 itself, is significantly lower than the magnitude of the Poynting vector associated with the light propagating through the diffusive medium 22. With less energy incident upon it, the metal slug 128 does not increase its temperature past the point at which heat-induced tissue damage occurs. Consequently, heat-induced tissue damage is avoided.

Figure 13:
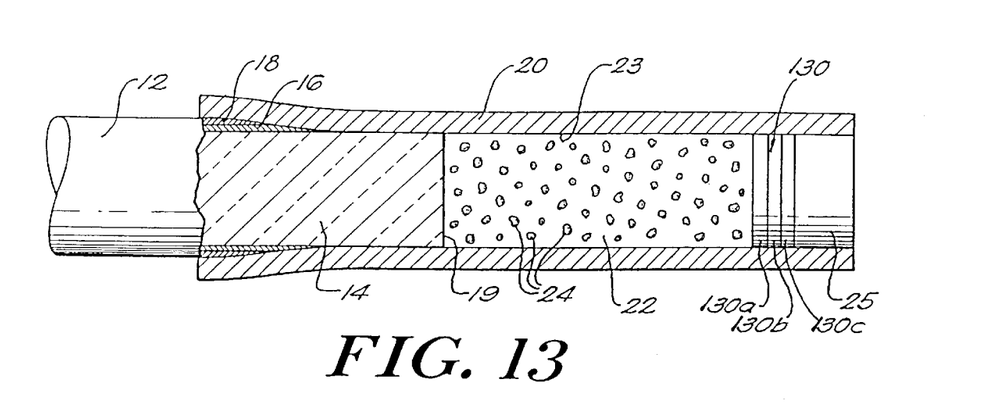
FIG. 13 is a close-up view of an alternative embodiment in which the metal slug shown in FIG. 12 is removed.

For applications in which it is unnecessary to monitor the position of the tip of the diffusive tip assembly, the metal slug 128 is not necessary and can be dispensed with as shown in FIG. 2. The reflecting function provided by the metal slug 128 in the embodiment shown in FIG. 1 is instead performed by the dielectric reflector 130. Since the dielectric reflector 130 is comprised of materials having no imaginary component of index of refraction, no absorptive heating occurs within it. As a result, the dielectric reflector 130 can prevent light from escaping through the distal end of the tubular chamber without a corresponding increase in temperature sufficient to cause heat damage to surrounding tissue.

Figure 14A:
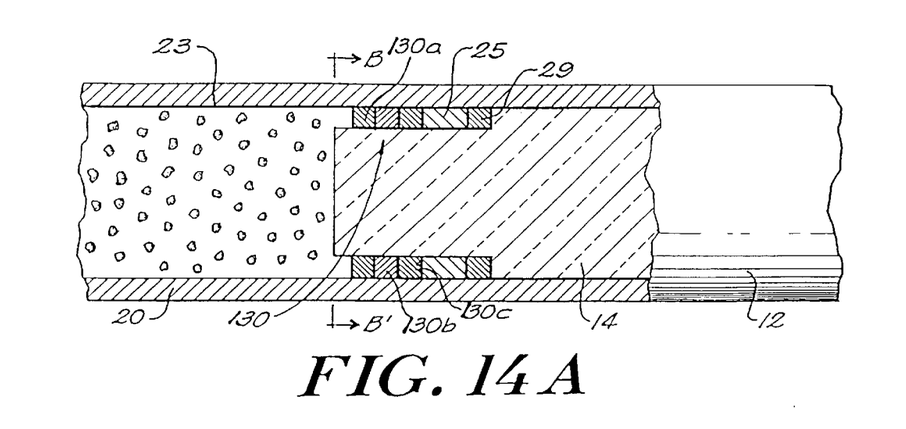
FIG. 14A shows an embodiment similar to that shown in FIG. 13 in which the metal slug, the glass substrate, and the plurality of dielectric layers are cylindrical and circumferentially disposed around the diffusive medium.
Figure 14B:
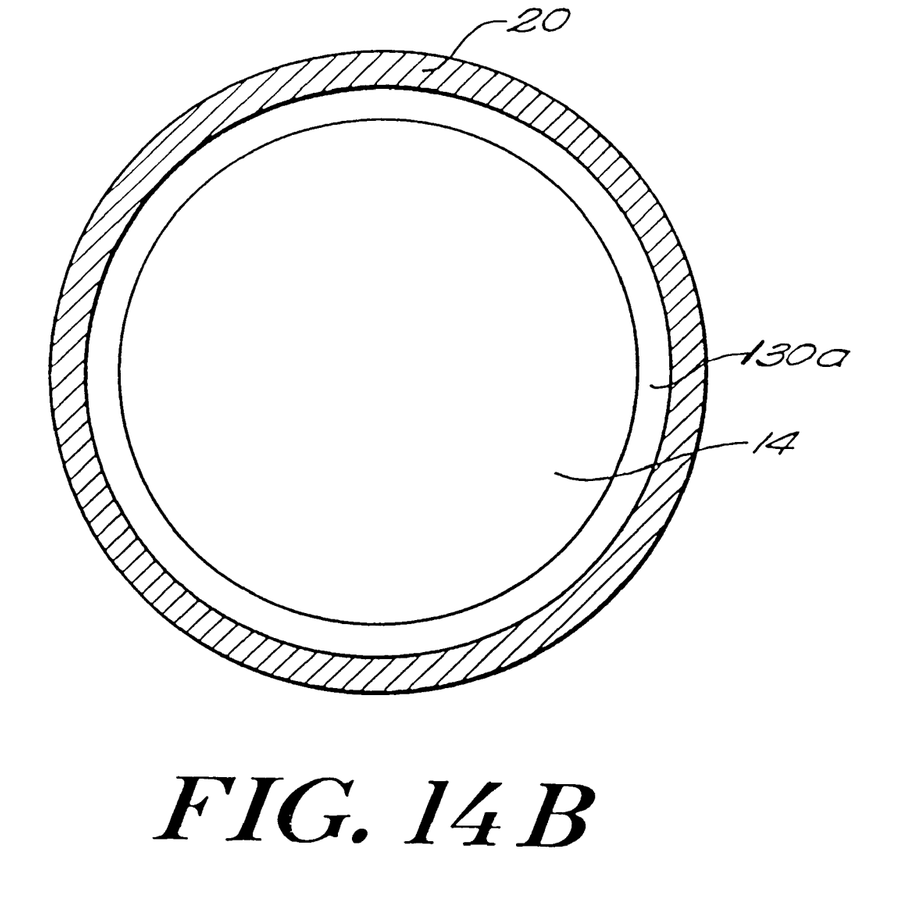
FIG. 14B is a cross-section of the structure depicted in FIG. 14A.

In certain endoscopic applications, it is also of interest to locate a point on the diffusive tip assembly other than the tip. For these applications, the dielectric reflector 130 can be an annular structure comprised of a series of dielectric layers 130a, 130b, 130c on an annular substrate layer 25 as shown in FIG. 3A and in cross-section in FIG. 3B. In this embodiment, a radiographic marker such as a metal collar 29 is adjacent to an annular substrate layer 25. The fiber optic core 14 extends into the interior of the annulus and into the diffusive medium 22 that fills the tubular chamber.

In the embodiment shown in FIGS. 14A and 14B, the undesired heating of the metal collar 29 is reduced by shielding it with a dielectric reflector 130 in the same manner as that described above in connection with FIG. 12. Since the dielectric reflector 130, like the metal collar 29, is annular, light can propagate through the center of the annulus formed by the dielectric reflector 130 and the metal collar 29 with minimal interference. Simultaneously, light incident on the metal collar 29 is significantly attenuated by the dielectric reflector 130. Consequently, the undesired heating of the metal collar 29 is reduced.

It will thus be seen that the invention efficiently attains the objects set forth above. Since certain changes may be made in the above construction without departing from the scope of the invention, it is intended that all matter contained in the above description or shown in the accompanying drawings be interpreted as illustrative and not limiting.

It is also to be understood that the following claims are intended to cover all generic and specific features of the invention described herein. When describing the invention, what is claimed as new and secured by Letters Patent is:

1. A diffusive tip assembly for use with an optical fiber for diffusion of radiation propagating through said fiber, the tip assembly comprising a light transmissive housing having a first end adapted to receive a light transmitting optical fiber and a second end with a reflective surface, and a light scattering medium disposed within the housing, wherein said scattering medium and said second end reflective surface interact to provide a substantially uniform axial distribution of radiation over the length of said tip assembly, such that radiation propagating through a fiber when connected to said assembly enters the scattering medium and a portion of the radiation is scattered outward through said housing, and another portion passes through the scattering medium and is reflected by the reflective surface for retransmission through said scattering medium.

2. The apparatus of claim 1 wherein the scattering medium further comprises a material having light scattering particles incorporated therein.

3. The apparatus of claim 2 wherein the particles are substantially uniformly dispersed throughout a polymeric material.

4. The apparatus of claim 3 wherein the polymeric material is a material selected from the group of silicone and epoxy polymers.

5. The apparatus of claim 2 wherein the scatterer medium is a liquid having light scattering particles incorporated therein.

6. The apparatus of claim 2 wherein the scatterer particles are chosen from the group consisting of alumina, silica, and titania compounds and mixtures thereof.

7. The apparatus of claim 1 wherein the housing further comprises radiation transmissive fluorocarbon polymer.

8. The apparatus of claim 1 wherein the reflective surface further comprises at least one mirror coated surface.

9. The apparatus of claim 8 wherein the mirror coated surface is coated with at least one dielectric layer.

10. The diffusive tip assembly of claim 9 wherein said at least one dielectric layer comprises a dielectric from a group consisting of rare earth oxides, silicon dioxide, titanium dioxide, and silica oxide.

11. The diffusive tip assembly of claim 9 wherein said at least one dielectric layer has an optical thickness equal to an integral number of quarter wavelengths, said wavelengths being measured within said at least one dielectric layer.

12. The diffusive tip assembly of claim 1 wherein said reflective surface further comprises a plurality of dielectric layers between about six and about thirty dielectric layers.

13. The diffusive tip assembly of claim 9 wherein said assembly further comprises an annular collar circumferentially disposed around said diffusive medium.

14. The apparatus of claim 1 wherein the apparatus further comprises a reflector means for effecting an exposure pattern having an azimuthal extent of less than 360°.

15. The apparatus of claim 14 wherein the reflector element is curved element disposed between two layers of said housing.

16. A method of phototherapy comprising the steps of placing a light diffusive assembly in proximity to a treatment site, the assembly comprising a light transmissive housing having a first end adapted to receive a light transmitting optical fiber and a second end with a reflective surface, and a light scattering medium disposed within the housing, wherein said scattering medium and said second end reflective surface interact to provide a substantially uniform axial distribution of radiation over the length of said tip assembly, such that radiation propagating through a fiber when connected to said assembly enters the scattering medium and a portion of the radiation is scattered outward through said housing, and another portion passes through the scattering medium and is reflected by the reflective surface for retransmission through said scattering medium, providing a source of therapeutic radiation to said diffusive assembly via an optical fiber connected to said first end, and activating said radiation source to effect treatment diffused radiation.

17. A method of phototherapy comprising the steps of placing a light diffusive assembly in proximity to a treatment site, the tip assembly comprising a light transmissive housing having a first end adapted to receive a light transmissive optical fiber, a light scattering medium disposed within the housing, and a reflector means longitudinally disposed in proximity to the house to shield a portion of the surrounding environment from irradiation, wherein said reflective means is coated with at least one dielectric layer, such that radiation propagating through a fiber when connected to said assembly enters the scattering medium and a portion of the radiation is scattered outward through said housing, yielding an exposure pattern having an azimuthal extent of less than 360°; providing a source of therapeutic radiation to said diffusive assembly via an optical fiber connected to said first end, and activating said radiation source to effect treatment diffused radiation.

18. The method of claim 17 wherein the method further comprises rotating same assembly to irradiate different azimuthal regions.

19. A diffusive tip assembly for use with an optical fiber for diffusion of radiation propagating through said fiber, the tip assembly comprising a light transmissive housing having a first end adapted to receive a light transmitting optical fiber and a second end with a mirror, wherein said mirror is coated with at least one dielectric layer, and a light scattering medium disposed within the housing, such that radiation propagating through a fiber when connected to said assembly enters the scattering medium and a portion of the radiation is scattered outward through said housing, and another portion passes through the scattering medium and is reflected by the mirror for retransmission through said scattering medium.

20. The diffusive tip assembly of claim 19, wherein said at least one dielectric layer comprises a dielectric from a group consisting of rare earth oxides, silicon dioxide, titanium dioxide, and silica oxide.

21. The diffusive tip assembly of claim 19, wherein said at least one dielectric layer has an optical thickness equal to an integral number of quarter wavelengths, said wavelengths being measured within said at least one dielectric layer.

22. The diffusive tip assembly of claim 19, wherein said mirror comprises a plurality of dielectric layers between about six and about thirty dielectric layers.

23. The diffusive tip assembly of claim 19, wherein said assembly further comprises an annular collar circumferentially disposed around said diffusive medium.

24. The diffusive tip assembly of claim 19 further comprising a reflector means for effecting an exposure pattern having an azimuthal extent of less than 360 degrees.

25. The diffusive tip assembly of claim 24, wherein said reflector means is a curved element disposed between two layers of said housing.

* * * * *

UNITED STATES PATENT AND TRADEMARK OFFICE
CERTIFICATE OF CORRECTION

| | | |
|---|---|---|
| PATENT NO. | : 6,270,492 B1 | Page 1 of 1 |
| DATED | : August 7, 2001 | |
| INVENTOR(S) | : Edward L. Sinofsky | |

It is certified that error appears in the above-identified patent and that said Letters Patent is hereby corrected as shown below:

Column 7,
Line 65, "SA, the longitudinal" should read -- 5A, the longitudinal --

Signed and Sealed this

Twelfth Day of March, 2002

*Attest:*

*Attesting Officer*

JAMES E. ROGAN
*Director of the United States Patent and Trademark Office*